United States Patent [19]

Gironda et al.

[11] Patent Number: 5,178,779
[45] Date of Patent: Jan. 12, 1993

[54] DEVICE FOR PROTECTING AGAINST CHEMICAL SPLASHING DUE TO BREAKAGE OF DISK FILTERS

[75] Inventors: Kevin F. Gironda, Alpha, N.J.; Francis T. Letterio, Philadelphia, Pa.

[73] Assignee: Rohm and Haas Company, Philadelphia, Pa.

[21] Appl. No.: 636,658

[22] Filed: Jan. 2, 1991

[51] Int. Cl.$^5$ .................... B01D 29/085; B01D 9/06
[52] U.S. Cl. .................... 210/800; 210/249; 422/101; 422/104
[58] Field of Search ............ 210/249, 767, 800; 422/100, 101, 104

[56] References Cited

U.S. PATENT DOCUMENTS

| | | | |
|---|---|---|---|
| 4,284,603 | 8/1981 | Karom | 422/101 |
| 4,346,057 | 8/1982 | Bowser | 422/101 |
| 4,642,220 | 2/1987 | Björkman | 422/101 |
| 4,832,842 | 5/1989 | Limb | 422/101 |
| 4,925,630 | 5/1990 | Grunwald | 422/104 |
| 4,963,493 | 10/1990 | Daftsios | 422/104 |

*Primary Examiner*—Robert A. Dawson
*Assistant Examiner*—W. L. Millard
*Attorney, Agent, or Firm*—Michael B. Fein

[57] ABSTRACT

Method and device for protecting against chemical spills due to breakage of disk filters use to filter chemicals comprising (A) a base having an upper surface with at least one vial well or groove adapted to allow sample vials to be inserted and to support said vials during a filter operation, said base having a front vertical shield portion at least as high as the top of the sample vials when said vials are inserted; (B) a rack having a rear side with at least one slot, each of said slots adapted to slidably engage the disk filter portion of a filter syringe apparatus and to prevent said disk filter from bursting during a filter operation, each of said slots positioned in said rack so that when said rack is fit on said base, every male portion of every disk filter which is engaged in one of said slots fits in a corresponding sample vial inserted in the corresponding vial well or groove.

6 Claims, 5 Drawing Sheets

DEVICE FOR PROTECTING AGAINST CHEMICAL SPLASHING DUE TO BREAKAGE OF DISK FILTERS

BACKGROUND OF THE INVENTION

1. Field of the Invention

This invention relates to the field of laboratory apparatus.

2. Description of the Prior Art

It is common in chemical laboratories to use disk filters screwed into syringes to filter liquid samples prior to analysis. Due to the fact that the disk filters are made in two parts with a seam around the outer periphery, sometimes the disk filters break or burst during a filter operation, causing spills or splashes which may harm the operator or the environment. One syringe-filter is used at a time to filter liquid. When several samples must be filtered, an operator must do one at a time.

SUMMARY OF THE INVENTION

It is an object of the present invention to prevent splashing or spills due to breakage of disk filters.

It is a further object to direct any spills or splashes of chemicals during a disk filtration operation away from the operator.

A further object is to provide a method of filtering using disk filters which prevents splashing of chemicals.

A still further object is to provide an apparatus or device for protecting against chemical splashing due to breakage of disk filters.

Another object is to provide a device which allows several disk filters to be used in one operation.

These objects, and other which will become apparent from the following disclosure, are achieved by the present invention which comprises in one aspect a device for protecting against chemical spills due to breakage of disk filters used to filter chemicals comprising (A) a base having an upper surface with at least one vial well or groove adapted to allow sample vials to be inserted and to support said vials during a filter operation, said base having a front vertical shield at least as high as the top of the sample vials when said vials are inserted; (B) a rack having at least one slot, each of said slot(s) adapted to slidably engage the disk filter portion of a filter syringe apparatus and to prevent said disk filter from bursting during a filter operation, each of said slots positioned in said rack so that when said rack is fit on said base, every male portion of every disk filter which is engaged in one of said slots fits in a corresponding sample vial inserted in the corresponding vial well or groove.

In another aspect the invention comprises a method of filtering using a disk filter-syringe apparatus so as to avoid spilling or splashing due to bursting of a disk filter comprising (A) sliding one or more disk filters in one or more slots of the above-described rack, (B) inserting one or more vials in the vial wells or grooves of the above-described base, (C) fitting the rack on the base so that the male portions of every disk filter fit in a corresponding sample vial.

DETAILED DESCRIPTION OF THE INVENTION

Figure 1:
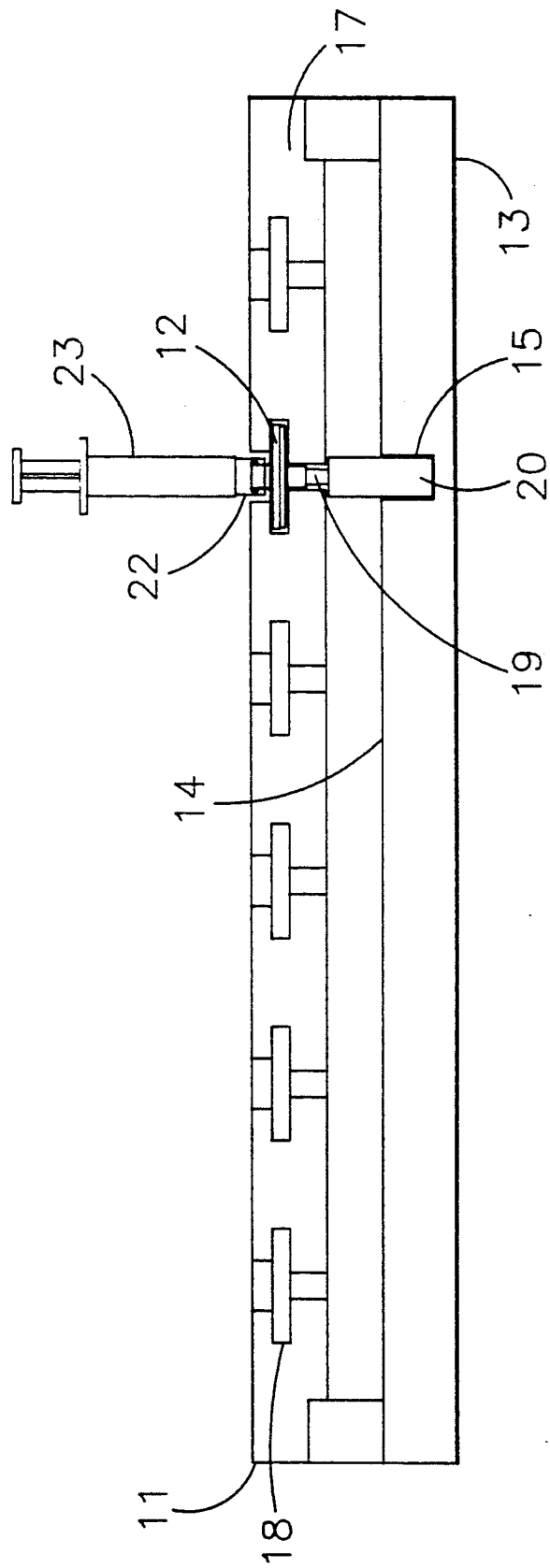
FIG. 1 is a rear elevational view of a rack and base, according to the invention, with a syringe, disk filter, and vial shown.
Figure 2:
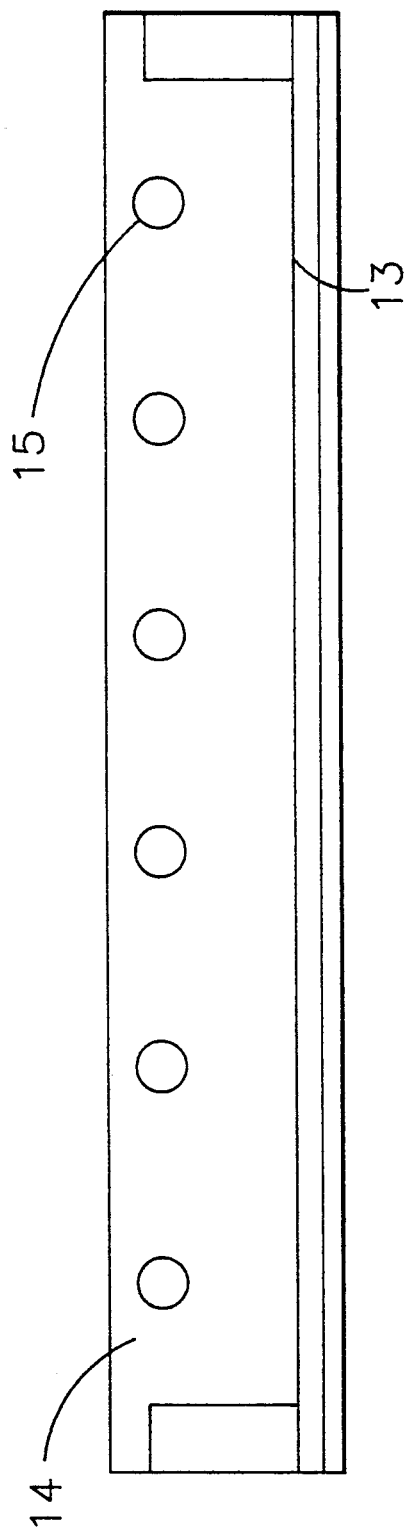
FIG. 2 is a top plan of a base portion of a device of the invention.
Figure 4:
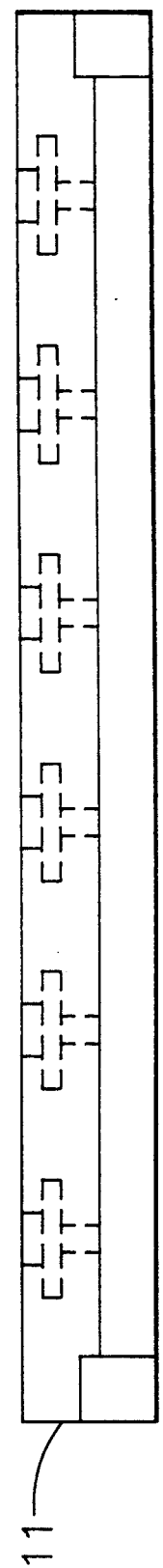
FIG. 4 is a front elevational view of a device of the invention.
Figure 3:
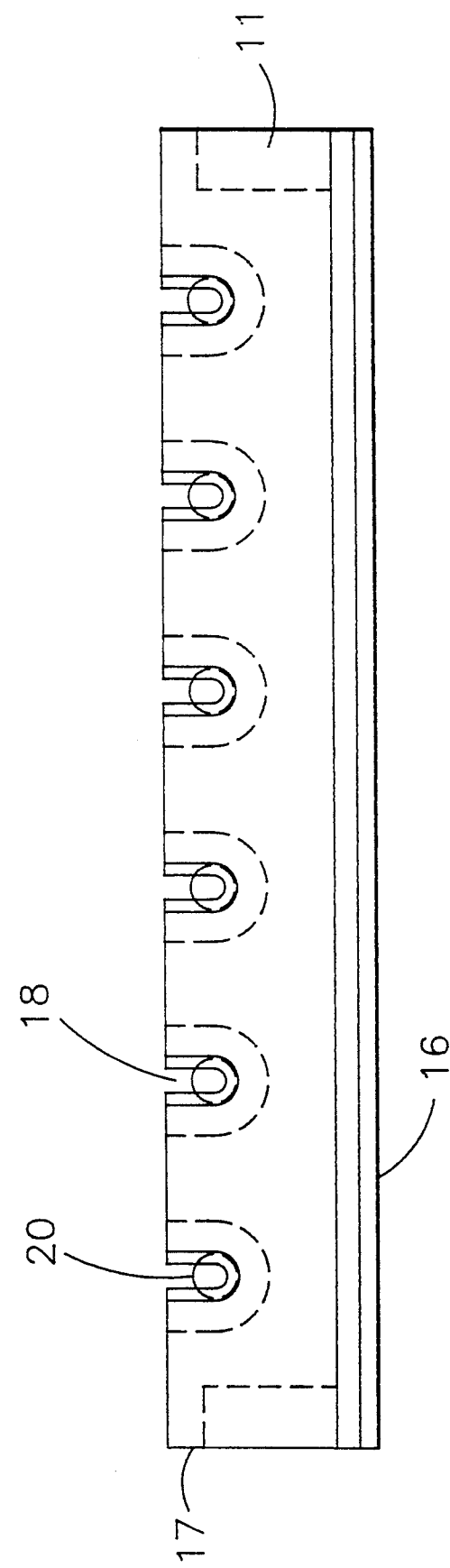
FIG. 3 is a top plan view of a rack of the invention.
Figure 5:
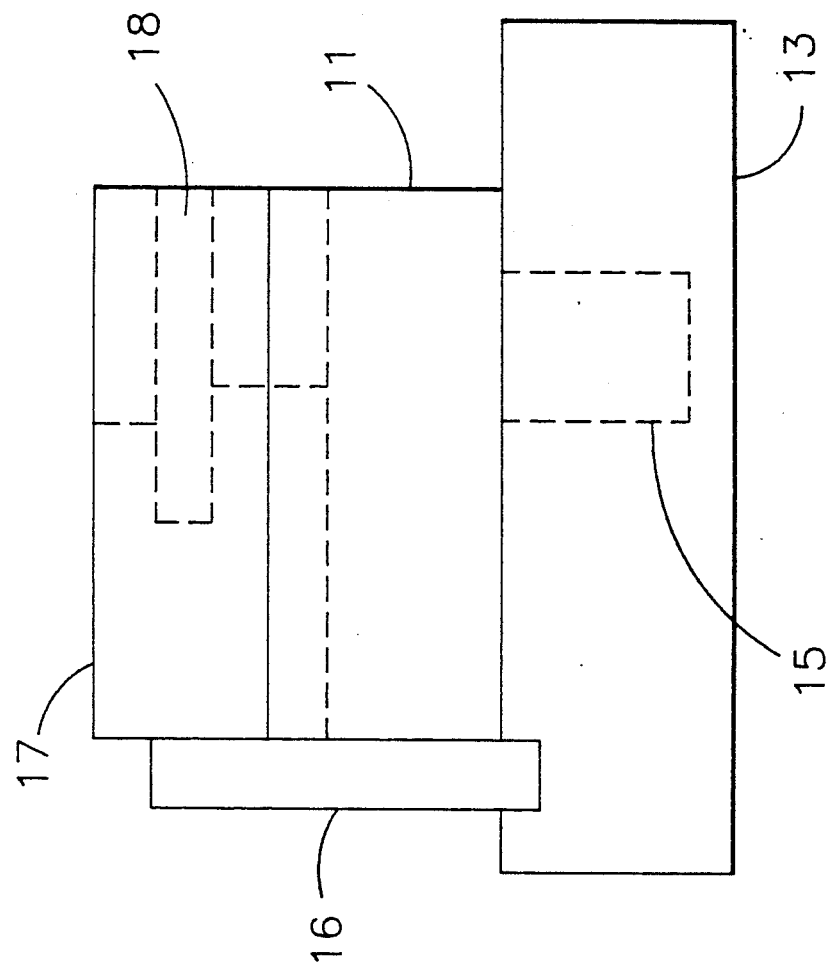
FIG. 5 is a side view of the device.
Figure 6:
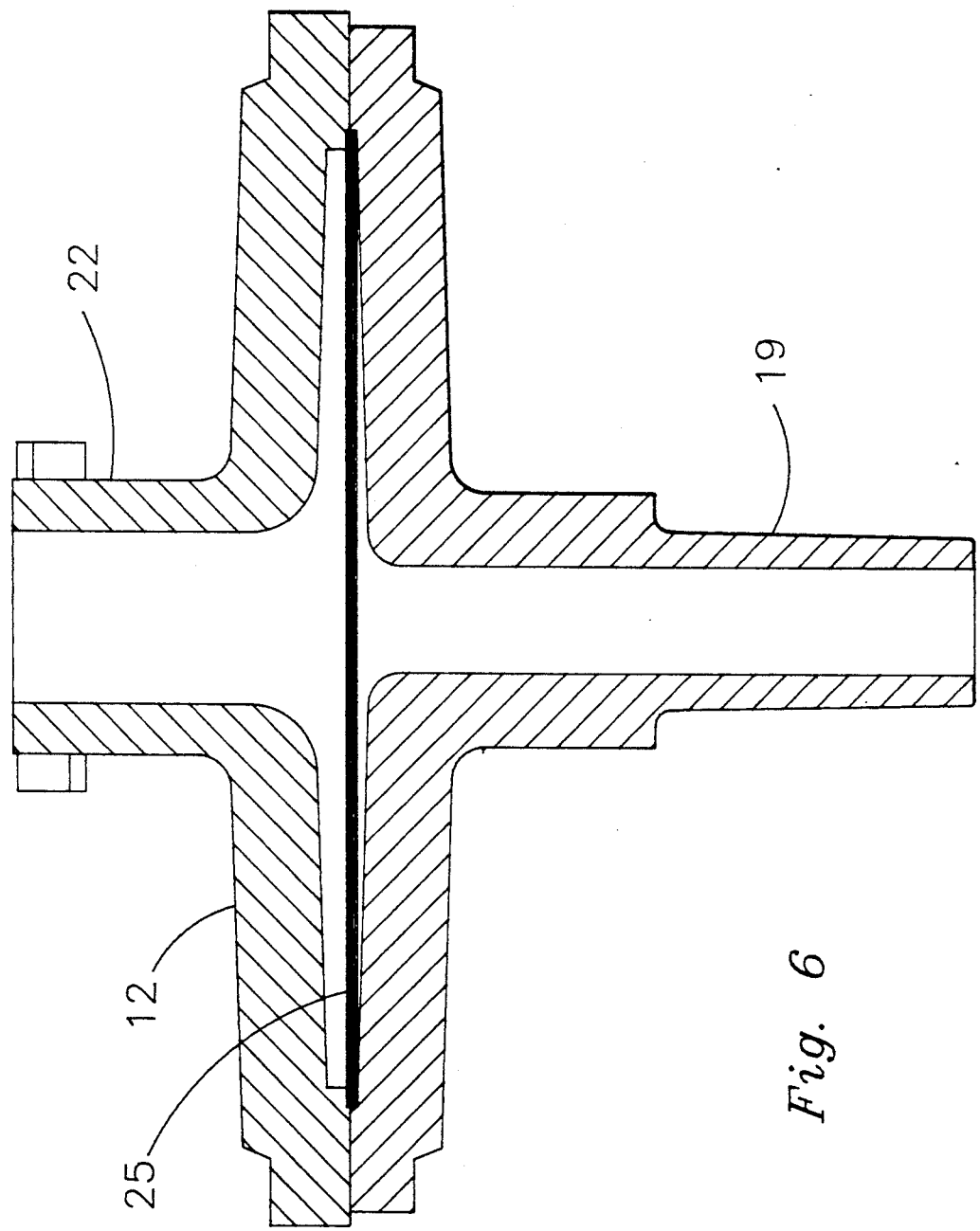
FIG. 6 is an elevational view of a disk filter having a seam.

According to the invention, a device 11 for protecting against chemical spills due to breakage of disk filters 12 used to filter chemicals comprising (A) a base 13 having an upper surface 14 with at least one vial well 15 or groove (not shown) adapted to allow sample vials to be inserted and to support said vials during a filter operation, said base having a front vertical shield 16 at least as high as the top of the sample vials when said vials are inserted; (B) a rack 17 having least one slot 18, each of said slots adapted to slidably engage the disk filter portion 12 of a filter syringe apparatus and to prevent said disk filter 12 from bursting during a filter operation, each of said slots 18 positioned in said rack 17 so that when said rack 17 is fit on said base, every male portion 19 of every disk filter which is engaged in one of said slots 18 fits in a corresponding sample vial 20 inserted in the corresponding vial well 15 or groove.

In operation, referring to FIG. 7, a syringe 23 is filled with a liquid 21 to be filtered, a disk filter 12 having a male threaded portion 22 is screwed into the syringe 23. The disk filter 12 has a male non-screw portion 19 which is designed to direct the filtrate 24 into a sample vial 20. Then the disk 12 is slidably engaged into the slot 18 of the rack 17. Other disks 12 may also be slid into other slots 18. Sample vials 20 are placed in the wells 15 or grooves of the base 13, the rack 17 is set in place on the base 13 so the male portion 19 of each disk 12 fits into a corresponding vial 20, and then the syringe 23 is depressed to filter the liquid 21. Filtrate 24 comes out the bottom outlet 19 of the disk filter 12 into the sample vial 20. The slot 18 of the rack 17 is constructed of a material, preferably clear acrylic plastic, so as to prevent the inserted disks 12 from breaking at the seams 25 when the pressure builds up during a filtering operation.

While the invention has been described with reference to specific examples and applications, other modifications and uses for the invention will be apparent to those skilled in the art without departing from the spirit and scope of the invention defined in the appended claims.

We claim:

1. Device for protecting against chemical spills due to breakage of disk filters used to filter chemicals comprising (A) a base having an upper surface with at least one vial well or groove adapted to allow sample vials to be inserted and to support said vials during a filter operation, said base having a front vertical shield at least as high as the top of the sample vials when said vials are inserted; (B) a rack having a rear side with at least one horizontal slot approximately the width and height of a disk filter, said horizontal slot adapted to slidably engage the disk filter portion of a filter syringe apparatus and to prevent said disk filter from bursting during a filter operation, said horizontal slot having a left side and a right side and an open vertical portion midway between said left side and said right side, said vertical portion approximately the width of a syringe and in a position such that when a filter disk with syringe attached is inserted in said rack from said rear side, said syringe fits within said vertical portion and said disk slidably engages said horizontal portion, each of said slots positioned in said rack so that when said rack is fit on said base, every male portion of every syringe attached to every disk filter which is engaged in one of said slots fits in a corresponding sample vial inserted in the corresponding vial well or groove.

2. Device according to claim 1 wherein said rack is adapted to removably engage said base.

3. Device according to claim 1 wherein said rack and said base are hinged so that said rack can be rotated away from said base for removal and insertion of disk filters.

4. Device according to claim 1 wherein said rack has two or more slots and said base has a corresponding number of grooves.

5. Device according to claim 1 wherein said rack has at least five slots and said base has a corresponding number and location of vial wells or grooves.

6. Method of filtering using a disk filter-syringe apparatus so as to avoid spilling or splashing due to bursting of disk filter comprising (A) sliding one or more disk filters of said disk filter-syringe apparatus in one or more slots of a second apparatus for protecting against chemical spills due to breakage of disk filters comprising a base having an upper surface with at least one vial well or groove adapted to allow sample vials to be inserted and to support said vials during a filter operation, said base having a front vertical shield at least as high as the top of the sample vials when said vials are inserted; and a rack having a rear side with one or more slots, each adapted to slidably engage the disk filter portion of a filter syringe apparatus and to prevent said disk filter from bursting during a filter operation, each of said slots positioned in said rack so that when said rack is fit on said base, every male portion of every disk filter which is engaged in one of said slots fits in a corresponding sample vial inserted in the corresponding vial well or groove;

(B) inserting one or more vials in the vial wells or grooves of the base of said device;

(C) fitting the rack on the base so that the male portions of every disk filter fit in a corresponding sample vial; and (D) compressing said syringes to filter the chemical samples into the corresponding vials.

* * * * *